United States Patent
Guzman-Carrazco et al.

(10) Patent No.: US 12,013,182 B2
(45) Date of Patent: Jun. 18, 2024

(54) METHOD FOR DRYING WET POLYMER COMPOSITION

(71) Applicant: SABIC GLOBAL TECHNOLOGIES B.V., Bergen op Zoom (NL)

(72) Inventors: Job Daniel Guzman-Carrazco, Geleen (NL); Aaron Seung-Joon Rhee, Geleen (NL); Miran Milosevic, Geleen (NL); Arash Helmi Siasi Faramani, Geleen (NL); Martin Van Sint Annaland, Geleen (NL); Ivo Roghair, Geleen (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 885 days.

(21) Appl. No.: 17/049,238

(22) PCT Filed: Apr. 5, 2019

(86) PCT No.: PCT/EP2019/058606
§ 371 (c)(1),
(2) Date: Oct. 20, 2020

(87) PCT Pub. No.: WO2019/206602
PCT Pub. Date: Oct. 31, 2019

(65) Prior Publication Data
US 2021/0239395 A1 Aug. 5, 2021

(30) Foreign Application Priority Data
Apr. 24, 2018 (EP) .................................... 18168951

(51) Int. Cl.
| | |
|---|---|
| F26B 3/084 | (2006.01) |
| B01J 8/32 | (2006.01) |
| C08F 6/12 | (2006.01) |
| C08K 3/36 | (2006.01) |
| F26B 17/00 | (2006.01) |

(52) U.S. Cl.
CPC ................ *F26B 3/084* (2013.01); *B01J 8/32* (2013.01); *C08F 6/12* (2013.01); *C08K 3/36* (2013.01); *F26B 17/00* (2013.01); *B01J 2208/00017* (2013.01)

(58) Field of Classification Search
CPC ... F26B 3/084; F26B 17/00; B01J 8/32; C08F 6/12; C08K 3/36
See application file for complete search history.

(56) References Cited

U.S. PATENT DOCUMENTS

| | | | |
|---|---|---|---|
| 3,654,705 | A | 4/1972 | Smith et al. |
| 5,200,477 | A | 4/1993 | Baker et al. |
| 8,124,697 | B2 | 2/2012 | Noble |
| 2008/0187756 | A1 | 8/2008 | Riegel et al. |
| 2009/0238916 | A1 | 9/2009 | Grawe et al. |

FOREIGN PATENT DOCUMENTS

| | | |
|---|---|---|
| JP | 0980803 A | 3/1997 |
| JP | 2005249897 A | 9/2005 |

OTHER PUBLICATIONS

DE 10251790 machine translation (Year: 2004).*
International Search Report for International Application No. PCT/EP2019/058606, International Filing Date Apr. 5, 2019, Date of Mailing Jul. 1, 2019, 4 pages.
Written Opinion for International Application No. PCT/EP2019/058606, International Filing Date Apr. 5, 2019, Date of Mailing Jul. 1, 2019, 7 pages.

* cited by examiner

*Primary Examiner* — Edward J Cain
(74) *Attorney, Agent, or Firm* — CANTOR COLBURN LLP

(57) ABSTRACT

The invention relates to a method for drying a wet polymer composition obtained from a polymerization process, comprising: a) introducing the wet polymer composition and a drying gas into a fluidized bed dryer to form a fluidized bed of the wet polymer composition and b) heating the fluidized bed to obtain a dry polymer composition, wherein the fluidized bed further comprises an anti-fouling agent comprising inert nanoparticles.

18 Claims, No Drawings

METHOD FOR DRYING WET POLYMER COMPOSITION

CROSS REFERENCE TO RELATED APPLICATIONS

This application is a National Stage application of PCT/EP2019/058606, filed Apr. 5, 2019, which claims the benefit of European Application No. 18168951.4, filed Apr. 24, 2018, both of which are incorporated by reference in their entirety herein.

The invention relates to a method for drying a wet polymer composition obtained from a polymerization process.

Several polymerization processes generate polymer powders and/or polymer cakes containing residual solvent. These wet (solvent-containing) polymer compositions are often dried in fluidized bed dryers. Fluidized bed dryers offer high rates of heat and mass transfer, but they are subjected to polymer fouling, particularly when they contain embedded heating elements. Polymer fouling in the dryers requires periodical cleaning, and it can cause unplanned shutdowns of the polymerization process, resulting in time and production losses.

Prior art to reduce polymer fouling in fluidized systems has focused on reducing polymer fouling in gas-phase polymerization reactors.

U.S. Pat. No. 5,200,477 describes the addition of an anti-fouling powder into a gas-phase reactor to reduce particle agglomeration and enable the production of sticky (medium-density) polymers.

U.S. Pat. No. 8,124,697 describes the addition of scouring balls to reduce particle agglomeration in the distribution grid of a fluidized-bed vessel, specifically a gas-phase polymerization reactor. The scouring balls act as mechanical cleaning agents, by bouncing inside the fluidized-bed vessel.

There is a demand in the art for a method to reduce fouling in fluidized bed dryers. Fluidized bed dryers contain features that are not present in gas-phase reactors. For instance, fluidized bed dryers may contain embedded heating element to facilitate drying. No heating elements are included into gas-phase reactors.

It is an objective of the present invention to provide a method for drying a wet polymer composition obtained from a polymerization process in which the above-described and/or other needs are met.

The present invention provides a method for drying a wet polymer composition obtained from a polymerization process, comprising:
a) introducing the wet polymer composition and a drying gas into a fluidized bed dryer to form a fluidized bed of the wet polymer composition and
b) heating the fluidized bed to obtain a dry polymer composition, wherein the fluidized bed further comprises an anti-fouling agent comprising inert nanoparticles.

It was surprisingly found that the reduction in polymer fouling is achieved by adding an anti-fouling agent comprising inert nanoparticles into the fluidized-bed dryer. It is noted that the addition of an anti-fouling agent into a gas-phase reactor is known from U.S. Pat. No. 5,200,477. However, a gas-phase reactor is fundamentally different from a fluidized-bed dryer in that substantially larger quantities of solvent are present in a fluidized-bed dryer and the physics of particle agglomeration are different. Further, a fluidized-bed dryer has internal components such as heating elements which are particularly susceptible to fouling and thus require prevention of fouling. A gas-phase reactor does not have such components and hence solving the problem of a fluidized-bed dryer would not be based on a solution for a gas-phase reactor.

The anti-fouling agent works by coating the surface of the polymer particles, preventing both the agglomeration of particles and the deposition of polymer particles on the surfaces of the components of the fluidized bed dryer such as internal heating elements. The anti-fouling agent also coats the hot metal surfaces of internal heating elements (when present), so that fouling on the heating elements is reduced.

According to an aspect of the invention, the present invention provides a method for drying a wet polymer composition obtained from a polymerization process, comprising:
the polymerization process to obtain the wet polymer composition comprising powders of a polymer and residual volatile hydrocarbons used during the polymerization process of the polymer,
a) introducing the wet polymer composition and a drying gas into a fluidized bed dryer to form a fluidized bed of the wet polymer composition and
b) heating the fluidized bed to obtain a dry polymer composition, wherein the fluidized bed further comprises an anti-fouling agent comprising inert nanoparticles.

Fluidized Bed Dryer

Fluidized bed dryers (FBDs) are per se well-known and used extensively for the drying of wet particulate and granular materials, and even slurries, pastes, and suspensions, that can be fluidized when they are put in contact with gases at a suitable velocity. FBDs are commonly used in processing many products such as chemicals, carbohydrates, foodstuff, biomaterials, beverage products, ceramics, pharmaceuticals, detergents and surface-active agents, polymers and resins.

A fluidized bed dryer is formed by passing a gas stream from the bottom of a column of particulate solids. At low gas velocities, the bed is static (packed). The bed of particles rests on a gas distributor plate. At high gas velocities, the solid particles are suspended in the gas and the bed is said to be fluidized.

The FBD may contain internal heating elements. The method according to the invention is particularly advantageous when the FBD contains internal heating elements, since the internal heating elements are particularly susceptible to fouling as the polymer particles soften at high temperatures.

The internal heating elements have a surface temperature during step b) which is below the melting point of the polymer in the wet polymer composition. Typically, for the drying of HDPE powder, the internal heating elements have a surface temperature ranging from 70 to 135° C., preferably 90 to 120° C., and most preferably 93 to 112° C. during step b). In normal operation, the heater temperature starts at the low end of the range. As polymer fouling on the heater occurs, it is necessary to increase the surface temperature of the heater to compensate for the loss of heat transfer capabilities caused by the fouling layer. Higher surface temperatures result in an increased fouling rate, which requires still higher surface temperatures that result in more fouling. Eventually, the heater temperature reaches the upper value of the temperature range. At this point, it is necessary to stop the dryer for cleaning. In general, the highest heater temperature needs to be kept below the melting point of the polymer, which for HDPE is approximately 135° C. Other polymers, including other types of polyethylenes, have higher or lower melting points.

In some embodiments, the method according to the invention is a continuous process in which a flow of the wet polymer composition is continuously supplied to the fluidized bed dryer and a flow of the dry polymer composition is continuously collected from the fluidized bed dryer. In other embodiments, the method according to the invention is a batch-process in which the wet polymer composition is supplied to the fluidized bed dryer and dried and the dry polymer composition is collected from the fluidized bed dryer.

Wet Polymer Composition

During the polymerization process of the polymer, volatile hydrocarbons are used for purposes well-known to the skilled person. A wet polymer composition is obtained by the process, which comprises powders of the desired polymer and residual volatile hydrocarbons. It will be appreciated that the wet polymer composition obtained from a polymerization process does not comprise the anti-fouling agent. The anti-fouling agent is not used during the polymerization process by which the wet polymer composition is obtained.

The wet polymer composition obtained from a polymerization process is dried by the method according to the invention. The wet polymer composition may typically be in the form of polymer cakes. The wet polymer composition comprises powders of a polymer and residual volatile hydrocarbons. The amount of the residual volatile hydrocarbons is reduced by the drying method to obtain a dry polymer composition.

The polymer in the wet polymer composition is not limited to any specific type. Typically, the wet polymer composition comprises powders of one or more polymers selected from the group consisting of polyolefins such as ethylene homopolymer, propylene homopolymer and copolymers made by co-polymerization of ethylene or propylene with linear alpha olefins or dienes. Examples of linear alpha olefins include 1-butene, 1-hexene, and 1-octene. Examples of dienes include ethylidene norbornene, vinyl norbornene, and 1,9-decadiene.

The polymer powder is itself a mixture of polymer particles of different sizes. The polymer powders have sizes in the range of micrometer, much larger than the anti-fouling agent. Typically, the polymer powders have d50 of 50 to 1000 µm, for example 100 to 500 µm, as determined by light scattering. An example of a suitable light scattering apparatus for determining d50 is ANALYSETTE 22 dry dispersion unit from Fritz international.

The residual volatile hydrocarbons may be of any known type used during the polymerization of the polymers in the polymer composition. Examples include residual co-monomers, linear alkanes, branched alkanes, cycloalkanes and mixtures thereof. The amount of the residual volatile hydrocarbons in the wet polymer composition may typically be 5 to 50 wt %. The amount of the polymer in the wet polymer composition may typically be 50 to 95 wt %.

Drying Gas

Preferably, the drying gas is selected from the group consisting of nitrogen, air, and $CO_2$. More preferably, the drying gas is nitrogen. Air, and other oxygen-containing gases, are used as the drying gas when the mixture of the wet composition and the drying gas is kept well away of explosive or potentially explosive compositions.

Anti-Fouling Agent

The anti-fouling agent is introduced into the fluidized bed dryer to form a fluidized bed together with the wet polymer composition.

Preferably, the amount of the anti-fouling agent is selected to be 0.1 to 5 wt %, most preferably 0.3 to 1.5 wt % of the dry polymer composition. The amount of the anti-fouling agent to be used with respect to the wet polymer composition can easily be calculated based on the amount of the polymer in the wet polymer composition.

The anti-fouling agent may be introduced into the fluidized bed dryer in any manner.

For example, the anti-fouling agent may be introduced into the fluidized bed dryer together with the drying gas. Alternatively or additionally, the anti-fouling agent may be introduced into the fluidized bed dryer together with the wet polymer composition. The anti-fouling agent may be introduced into the fluidized bed dryer as a mixture with the wet polymer composition. The anti-fouling agent may be introduced in a polymerization reactor for preparing the wet polymer composition located upstream of the fluidized bed dryer to form a mixture with the wet polymer composition, which mixture is then introduced to the fluidized bed dryer.

In some embodiments, the method according to the invention is a continuous process and the anti-fouling agent is introduced into the fluidized bed dryer together with the wet polymer composition.

In some embodiments, the method according to the invention is a continuous process and the anti-fouling agent is introduced into the fluidized bed dryer together with the drying gas.

In some embodiments, the method according to the invention is a batch process and the anti-fouling agent is introduced into the fluidized bed dryer together with the wet polymer composition.

In some embodiments, the anti-fouling agent is introduced into the fluidized bed dryer before step a) and the anti-fouling agent is not introduced into the fluidized bed dryer during or after steps a) and b). This method may be a continuous process or a batch process.

In some embodiments, the method according to the invention further comprises the steps of:
c) removing the dry polymer composition obtained by step b) from the fluidized bed dryer and cooling the fluidized bed dryer,
d) introducing a further wet polymer composition obtained from a polymerization process and a further drying gas into the fluidized bed dryer to form a further fluidized bed of the further wet polymer composition and
e) heating the fluidized bed to obtain a further dry polymer composition, wherein the anti-fouling agent is not introduced into the fluidized bed dryer after step b).

In these embodiments, a further dry polymer composition is obtained without a further introduction of the anti-fouling agent. The further wet polymer composition may be the same as the wet polymer composition of step a). The further drying gas may be the same as the drying gas of step a).

The anti-fouling agent comprises inert nanoparticles. Nanoparticles tend to form loose aggregates that crumble under shear. It is understood that the anti-fouling agent comprises inert nanoparticles even if detectable aggregates are beyond the nanometer range. The inert characteristic refers to the lack of spontaneous chemical reactions in the temperature range of interest.

In the fluidized bed, the anti-fouling agent adheres to the much bigger polymer particles. Adhesion occurs on the polymer surface that is most sticky, rendering the entire polymer particles less sticky after partial coating. This can be determined e.g. by observation using scanning electron microscope, which also shows that the inert nanoparticles have sizes in the nanometer range.

Preferably, the inert nanoparticles have a primary particle size of about 1 to 100 nm and an average size of aggregate (primary structure) of 0.01 to 10 μm.

Examples of the inert nanoparticles useful in this invention include nanoparticles of fumed silica, carbon black and organoclay.

In some embodiments, the anti-fouling agent comprises a hydrophobic coating provided on the inert nanoparticles. This is advantageous if the anti-fouling agent is expected to enter a polymerization reactor located upstream or downstream of the fluidized bed dryer. The anti-fouling agent may also have an anti-fouling effect in the polymerization reactor.

The hydrophobic coating may comprise polydimethylsiloxane, such as the organo-modified polydimethylsiloxane described in U.S. Pat. No. 5,200,477. U.S. Pat. No. 5,200,477 is incorporated herein by reference, in particular the description of the organo-modified polydimethylsiloxane.

In some embodiments, the anti-fouling agent consists of the inert nanoparticles, thus without any coating or other pre-treatments. This is economically advantageous as it reduces the cost of the anti-fouling agent.

It is noted that the invention relates to all possible combinations of features described herein, preferred in particular are those combinations of features that are present in the claims. It will therefore be appreciated that all combinations of features relating to the method according to the invention are described herein.

It is further noted that the term 'comprising' does not exclude the presence of other elements. However, it is also to be understood that a description on a product/composition comprising certain components also discloses a product/composition consisting of these components. The product/composition consisting of these components may be advantageous in that it offers a simpler, more economical process for the preparation of the product/composition. Similarly, it is also to be understood that a description on a process comprising certain steps also discloses a process consisting of these steps. The process consisting of these steps may be advantageous in that it offers a simpler, more economical process.

The invention is now elucidated by way of the following examples, without however being limited thereto.

Experimental Part

A fluidized bed dryer (FBD) was used to dry a polymer cake. The polymer cake was a solid mixture of polymer powder and residual volatile hydrocarbons. The goal of drying was to remove the volatiles hydrocarbons to concentrations below 1% (The initial hydrocarbon concentration, before drying, can be as high as 50%). Drying was accomplished by two processes 1) fluidizing the cake with an inert drying gas and 2) heating the fluidized bed using embedded heating elements. Such type of FBD with embedded heating elements is commercially available from different suppliers. In the examples below, a purposely-built, lab-scale FBD containing one internal heating element was used. The purposely-build, lab-scale FBD allows detailed monitoring of controlled fouling experiments. The body of the FBD is a stainless steel (316 SS) vessel with a diameter of 45 mm and an L/D ratio of 12. The heating element was an electric cartridge heater (6.5 mm×75 mm 150 W, 120 V AC) connected to a power supply unit (EA-PS 8000T) from Elektro-Automatik. The temperature at the surface of the heater was measured by two thermocouples placed on the surface of the heater. Two interconnected temperature control loops connected to a PID controller (PLC software) were used to maintain the temperature at the surface of the cartridge heater at a desired value, typically 110° C.

The drying gas, entering from the bottom of the FBD, was nitrogen. The flow of nitrogen was set to maintain a gas velocity equal to three times the minimum fluidization velocity of the polymer power. The polymer powder was a bimodal HDPE powder produced by SABIC and sold (in pellet form) under the trade name of SABIC® Vestolen A 6060. The polymer powder has an average particle size (D50) of 180 micrometers, an intrinsic density of 950 kg/m3, and a minimum fluidization velocity of 1.5 cm/s.

In all the examples described below, the surface temperature of the heating element was maintained at 110° C., and a fluidized bed (made of nitrogen and HDPE powder and any silica) was stabilized and maintained in contact with the hot heater element for 1 hour. After the 1-hour period, the FBD was cooled down and the heating element was removed. The degree of fouling was determined from the mass of polymeric material deposited on the heater.

EXAMPLES

Comparative Example 1—HDPE Powder with No Antifouling Additives

A crust of polymeric material was deposited on the cartridge heater after 1-hour of exposure at 110° C. The polymeric material was brushed off and collected for further analysis. The mass of polymeric material was 6 grams.

Example 2—HDPE Powder with 0.5 Weight Percent of Hydrophobic Fumed Silica

HDPE powder was mixed with fumed silica and the resulting powder mixture was fluidized and put in contact with a hot heating element under the same conditions used for Example 1. A thin layer of polymer powder was deposited on the heating element. The polymeric material was brushed off and collected for further analysis. The mass of polymeric material was 1.4 grams.

Example 3—HDPE Powder with 1 Weight Percent of Hydrophobic Fumed Silica

HDPE powder was mixed with fumed silica and the resulting powder mixture was fluidized and put in contact with a hot heating element under the same conditions used for Example 1. A thin layer of polymer powder was deposited on the heating element. The polymeric material was brushed off and collected for further analysis. The mass of polymeric material was 0.5 grams.

Scanning electron microscopy (SEM) of the powders used in Examples 1, 2, and 3 revealed that, when present, fumed silica partially coats the surface of the polymer particles. The partial coating reduces the adhesion of the polymer particles, and their deposition onto hot surfaces. Compositional analysis of the material deposited on the heater surface indicated a relatively high concentration of fumed silica in the fouling material. In addition to partially coating the polymer particles, fumed silica also partially coats the surface of the heating elements, further reducing the deposition of polymer particles onto the heater.

The results are summarized in Table 1.

TABLE 1

|  | Anti-fouling agent | Amount of anti-fouling agent | Amount of fouling material (g) | Decrease in fouling |
|---|---|---|---|---|
| CE1 | none | 0 | 6.00 |  |
| E2 | hydrophobic fumed silica | 0.5 wt % | 1.41 | 77% |
| E3 | hydrophobic fumed silica | 1 wt % | 0.54 | 91% |

Based on the mass of polymeric material deposited on the heater, 0.5% of fumed silica reduced fouling by 77%, 1% of fumed silica reduced fouling by 91%.

Example 4—Introduction of Hydrophobic Fumed Silica Only in the Beginning

A heating element coated with fumed silica and polymer powder was obtained by repeating the conditions of Example 2 (loading polymer with 0.5 wt % silica), but without brushing off any deposited material from the surface of the heater at the end of the heating cycle.

After this initial step, the coated heating element was removed from the equipment; the equipment was fully opened and cleaned to remove any traces of fumed silica and polymer powder. The coated heating element was reintroduced into the equipment along with a new load of fresh polymer powder containing no fumed silica. The silica-free polymer powder was fluidized and heated for 1 hour, and the degree of fouling was determined by measuring the amount of material deposited on the heater.

The mass of polymeric material deposited on the heater after two heating cycles was 3.0 grams. This surprising result indicates that the amount of fouling per heating cycle is comparable (1.4 grams for the first cycle, 1.6 grams for the second one), even though no silica was added with the polymer on the second cycle. Therefore, fouling can be reduced by passivating the heater elements with an initial load of fumed silica, without necessarily adding extra silica to dry more powder in subsequent drying cycles.

The invention claimed is:

1. A method for drying a wet polymer composition obtained from a polymerization process, comprising:
   a) introducing the wet polymer composition and a drying gas into a fluidized bed dryer to form a fluidized bed of the wet polymer composition and
   b) heating the fluidized bed to obtain a dry polymer composition,
   wherein the fluidized bed further comprises an anti-fouling agent comprising inert nanoparticles,
   wherein the wet polymer composition comprises powders of one or more polymers selected from the group consisting of polyolefins.

2. The method according to claim 1, wherein the fluidized bed dryer contains internal heating elements.

3. A method according to claim 1, wherein the wet polymer composition comprises powders of a polymer and residual volatile hydrocarbons used during the polymerization of the polymer, wherein the amount of the residual volatile hydrocarbons in the wet polymer composition is 5 to 50 wt %.

4. The method according to claim 1, wherein the drying gas is selected from the group consisting of nitrogen, air and carbon dioxide.

5. The method according to claim 1, wherein the amount of the anti-fouling agent is 0.1 to 5 wt %, of the dry polymer composition.

6. The method according to claim 1, wherein the inert nanoparticles are selected from the group consisting of fumed silica, carbon black and organoclay.

7. The method according to claim 1, wherein the anti-fouling agent consists of the inert nanoparticles or the anti-fouling agent comprises a hydrophobic coating provided on the inert nanoparticles.

8. The method according to claim 1, wherein the method is a continuous process in which a flow of the wet polymer composition is continuously supplied to the fluidized bed dryer and a flow the dry polymer composition is continuously collected from the fluidized bed dryer.

9. The method according to claim 8, wherein the anti-fouling agent is introduced into the fluidized bed dryer together with the wet polymer composition.

10. The method according to claim 8, wherein the anti-fouling agent is introduced into the fluidized bed dryer together with the drying gas.

11. The method according to claim 1, wherein the method is a batch-process in which the wet polymer composition is supplied to the fluidized bed dryer and dried and subsequently the dry polymer composition is collected from the fluidized bed dryer.

12. The method according to claim 11, wherein the anti-fouling agent is introduced into the fluidized bed dryer together with the wet polymer composition.

13. The method according to claim 1, further comprising the polymerization process to obtain the wet polymer composition.

14. The method according to claim 1, wherein the anti-fouling agent is introduced into the fluidized bed dryer before step a) and the anti-fouling agent is not introduced into the fluidized bed dryer during or after steps a) and b).

15. The method according to claim 2, wherein the internal heating elements have a surface temperature during step b) of from 70° C. to below the melting point of polymer in the wet polymer composition.

16. The method according to claim 1, where the wet polymer composition comprises powders of one or more polymers selected from the group consisting of ethylene homopolymer, propylene homopolymer, and copolymers of ethylene or propylene with linear alpha olefins or dienes.

17. The method according to claim 5, wherein the amount of the anti-fouling agent is 0.3 to 1.5 wt %, of the dry polymer composition.

18. A method for drying a wet polymer composition obtained from a polymerization process, comprising:
   a) introducing the wet polymer composition and a drying gas into a fluidized bed dryer to form a fluidized bed of the wet polymer composition and
   b) heating the fluidized bed to obtain a dry polymer composition,
   wherein the fluidized bed further comprises an anti-fouling agent comprising inert nanoparticles,
   wherein the wet polymer composition comprises powders of a polymer and residual volatile hydrocarbons used during the polymerization of the polymer, wherein the amount of the residual volatile hydrocarbons in the wet polymer composition is 5 to 50 wt %.

* * * * *